United States Patent [19]

Ohki et al.

[11] 4,347,844
[45] Sep. 7, 1982

[54] POROUS SHEET AND PROCESS FOR PREPARATION THEREOF

[75] Inventors: Kenji Ohki; Mistru Tokuyama, both of Utsunomiya; Masayuki Sagae, Ichikaimachi; Kenji Kawabuchi, Wakayama, all of Japan

[73] Assignee: Kao Soap Co., Ltd., Tokyo, Japan

[21] Appl. No.: 220,395

[22] Filed: Dec. 29, 1980

[30] Foreign Application Priority Data

Jan. 10, 1980 [JP] Japan ................................. 55-1541

[51] Int. Cl.$^3$ .............................................. A61F 5/44
[52] U.S. Cl. ................................... 128/287; 428/325; 428/327; 428/331; 428/323; 156/77; 156/229; 428/338

[58] Field of Search ............... 428/325, 327, 330, 331, 428/306, 909; 106/122; 521/50; 128/287

[56] References Cited

U.S. PATENT DOCUMENTS

| | | | |
|---|---|---|---|
| 3,597,297 | 8/1971 | Buchholtz et al. | 428/17 |
| 3,844,865 | 10/1974 | Elton et al. | 428/330 |
| 3,983,287 | 9/1976 | Goossen et al. | 48/909 |

Primary Examiner—George F. Lesmes
Assistant Examiner—B. K. Johnson
Attorney, Agent, or Firm—Blanchard, Flynn, Thiel, Boutell & Tanis

[57] ABSTRACT

A porous sheet comprising a flexible sheet in which a rigid substance is incorporated, wherein pores are formed in the sheet by breaking the rigid substance.

7 Claims, 7 Drawing Figures

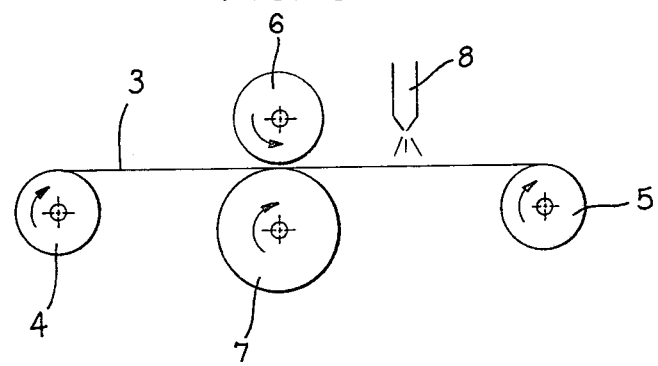
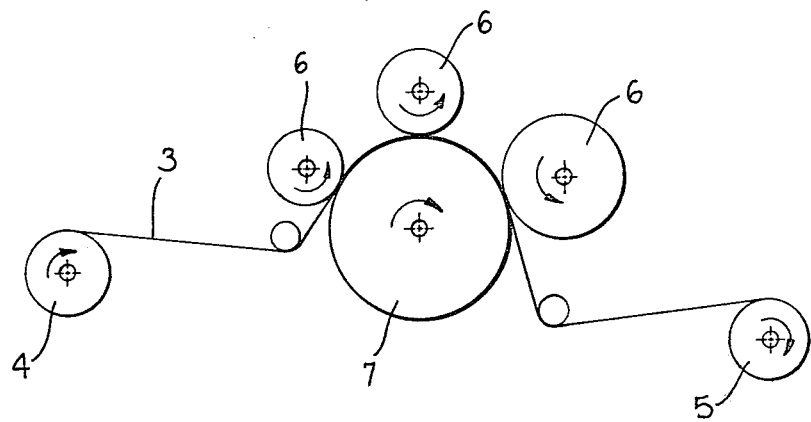

POROUS SHEET AND PROCESS FOR PREPARATION THEREOF

The present invention relates to a porous sheet and a process for the preparation thereof. More particularly, the present invention relates to a liquid-impermeable, vapor-permeable porous sheet and a process for the preparation thereof.

Recently, disposable diapers have been used as diapers for infants. Disposable diapers now being marketed are improved over cloth diapers in convenience and comfort, but they are still insufficient in some points. First of all, it can be mentioned that diaper dermatitis can occur as a result of wearing disposable diapers, although it is not a result inherently caused by the wearing of disposable diapers. It is eagerly desired to minimize or eliminate the occurrence of diaper dermatitis on wearing of disposable diapers. It is believed that the occurrence of diaper dermatitis is due to the use of a liquid-impermeable material as the back sheet, that is, the outermost layer, of the disposable diaper for inhibiting passage of the liquid to the outside and preventing contamination of the outside. Of course, this liquid impermeability is necessary as one function of the diaper. However, from the viewpoint of preventing the occurrence of a rash on the skin, it is preferred to use a back sheet that not only is liquid impermeable, but also is vapor permeable. A sheet having these properties in combination is conventionally prepared from a porous sheet having a great number of fine pores. As the methods now adopted for the manufacture of such porous sheets, there can be mentioned a method in which a film is perforated by electric discharge, a method in which a film containing a filler is drawn, and a method in which a film containing a filler is prepared and the filler is removed from the film. However, sheets prepared according to these conventional methods are not suitable for the manufacture of disposable products because the manufacturing cost is high or the strength is insufficient.

It is therefore a primary object of the present invention to provide a liquid-impermeable, vapor-permeable, porous sheet applicable to disposable products, which sheet can be manufactured very easily at a low cost, and also to provide a process for the preparation of such a porous sheet.

In accordance with the present invention, there is provided a porous sheet comprising a flexible sheet in which a rigid substance is incorporated, and wherein the pores are formed by breakage of the rigid substance.

The porous sheet according to the present invention and the process for the preparation thereof will now be described in detail.

BRIEF DESCRIPTION OF THE DRAWINGS

FIGS. 6 and 7 are flow diagrams showing the steps of embodiments of the process for the preparation of porous sheets according to the present invention.

Figure 1:
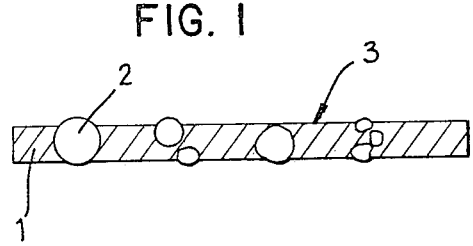
FIG. 1 is an enlarged sectional view showing an example of the filler-containing sheet that is used in the present invention.
Figure 2:
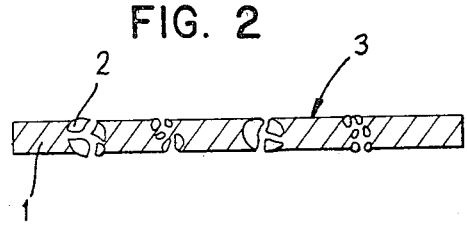
FIG. 2 is an enlarged sectional view showing a porous sheet of the present invention obtained by compressing the sheet shown in FIG. 1.

Filler-containing sheets are well known. In the present invention, a filler-containing sheet is used. More specifically, a filler-containing sheet 3 comprising a flexible sheet 1 and filler particles 2 incorporated in the flexible sheet 1, as shown in FIG. 1, is used in the present invention. When a compressive force is applied to this filler-containing sheet 3, the filler particles 2 are cracked or broken, as shown in FIG. 2, and many pores are formed penetrating through the filler-containing sheet 3 from the front face to the back face. Since the thus-formed pores are very fine or small in size, the resulting porous sheet is ordinarily rendered liquid-impermeable and vapor-permeable. When there is a possibility of liquid leakage through the sheet owing to the material of the filler or the pore size, the intended object of the invention can be attained by subjecting the resulting porous sheet to a treatment with a water repellent.

The flexible sheet 1 that is used in the present invention is a sheet that is not easily broken under application of a compressive force or stress, but it can easily be folded or bent. As the flexible sheet 1, there can be used a film of polyethylene or nylon and spun-bonded polyethylene or polyester. The rigid substance 2 used in the present invention comprises filler particles which can be incorporated into such a flexible sheet and which are broken under application of a compressive force or stress. For example, there can be mentioned beads and particles of glass, polystyrene, zeolite, silica, calcium carbonate, polypropylene, polytetrafluoroethylene and barium sulfate. The shape of the filler particles 2 is not particularly limited to a spherical shape, and the filler particles can have, for example, a needle-like shape and they can have a porous or hollow structure. From the viewpoint of the property of being easily broken, it is preferred that (A) the upper limit of the diameter of the filler particles 2 be the sum of the thickness of the flexible sheet plus 60 microns and (B) the lower limit of the diameter of the filler particles be 1 micron. When filler particles having a diameter close to this lower limit are to be broken, it is necessary that the filler particles 2 should be incorporated in the sheet in a clustered entirely or partially overlapping state, as shown in FIGS. 1 and 2 for the smaller size filler particles shown therein. Since the shape of the filler particles is not particularly limited to a spherical shape, the diameter referred to herein is the so-called corresponding diameter which is equal to the cube root of the valve obtained by dividing the volume of the filler particles by $\pi/6$.

When a hydrophilic substance, such as glass or silica, is used as the filler, the water resistance, that is, the resistance of the sheet to the passing of water therethrough, becomes insufficient. In this case, a porous sheet possessing excellent water resistance can be obtained by treating such filler with a water-repelling material, such as a silicone emulsion or tetrafluoroethylene. A known method, such as spraying or dipping, can be adopted for the water-repelling treatment.

Figure 3:
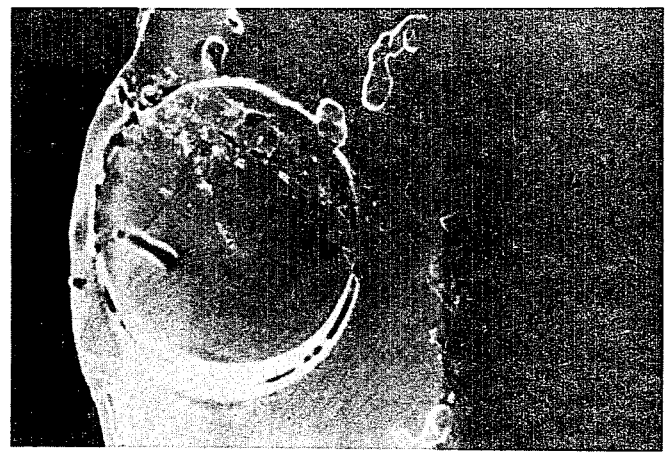
FIG. 3 is a microscope photograph of the section of an example of the filler-containing sheet that is used in the present invention.
Figure 4:
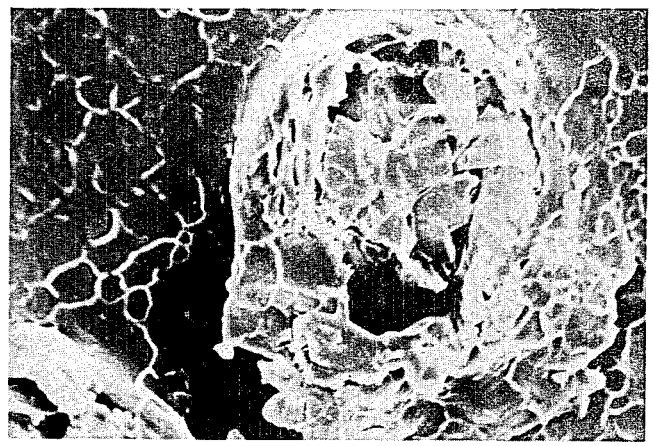
FIG. 4 is a microscope photograph of the top surface of a porous sheet of the present invention obtained by compressing the sheet shown in FIG. 3.
Figure 5:
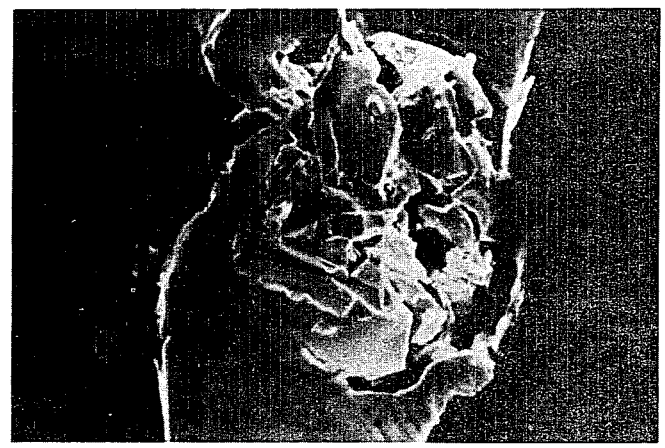
FIG. 5 is a microscope photograph of the section of the porous sheet shown in FIG. 4.

For better illustration of the present invention, microscope photographs of the sheet according to the present invention are shown in FIGS. 3, 4 and 5. FIG. 3 is a microscope photograph of the section of a low density polyethylene sheet in which glass beads having a diameter of 44 microns are incorporated, as the filler. FIG. 4 is a microscope photograph of the top plan of a porous sheet obtained by compressing the sheet shown in FIG. 3 under a pressure of 40 kg/cm² at room temperature. FIG. 5 is a microscope photograph of the section of the porous sheet shown in FIG. 4. Especially from FIG. 5, it will readily be understood that fine pores are formed, which pores extend from the front face to the back face of the sheet.

From the viewpoints of the ease of the operation and the productivity, a process comprising compressing a filler-containing sheet to break apart the filler is most preferred as the process for perparing the porous sheet of the present invention.

FIG. 6 is a flow diagram showing the steps of the preparation process using a pair of upper and lower pressing rollers. A filler-containing sheet 3 wound on a feed roller 4 is delivered out and is wound on a take-up roller 5. During its travel, the filler-containing sheet 3 is compressed between a pair of upper and lower pressing rollers 6 and 7 disposed intermediate between the rollers 4 and 5, whereby the filler particles are broken. If desired, a water-repelling solution may be sprayed on the sheet from a nozzle 8. The nozzle can be disposed either before or after the compressing step. The process shown in FIG. 6 is effective when the variation of the sizes of the filler particles is relatively small and the size of the filler is about 10 microns. When the variation of the sizes of the filler particles is large, the process shown in FIG. 7 is preferably adopted. The process shown in FIG. 7 is substantially the same as the process shown in FIG. 6, but is different from the process shown in FIG. 6 in the point that a plurality of upper pressing rollers 6 of different diameters are used. Accordingly, even if the particle size distribution range of the filler particles is wide, the respective filler particles can be broken by any one of the rollers 6 suitable for the particle sizes.

In the porous sheet of the present invention having the above-mentioned structure, the moisture permeability can easily be controlled by changing the quantity and the size of the filler particles and the compressing conditions. As compared with the porous sheet obtained by the stretching method, the porous sheet of the present invention is advantageous in that the reduction of the strength is small and the balance of the strength in the machine direction and the cross or transverse machine direction is good.

The present invention will now be described in detail with reference to the following Examples that by no means limit the scope of the invention. In the Examples, all reference to "%" mean percent by weight unless otherwise indicated.

EXAMPLE 1

Glass beads of E-glass having a particle size of 10 to 60 microns (GB731 manufactured by Toshiba-Ballotini) were incorporated into low density polyethylene (Sumikathene F-403-1 manufactured by Sumitomo Chemical Co.) having a weight average molecular weight of 9300, a melt index of 5 and a melting point of 109° C. at a mixing ratio as indicated below, and the glass bead-containing polyethylene was formed into a film hving a thickness of 20 microns by the T-die method. The film was compressed and dipped in a 2% solution of a fluorine type emulsion (FC-453-30 manufactured by Sumitomo-3 M). The amount applied of the emulsion was 5%. The properties of the thus-obtained sheets are shown in Table 1 (Runs Nos. 1 to 15). In another experiment, a 30% solution of a silicone emulsion (Horn X-51-296 manufactured by Shinetsu Silicone) was used instead of the fluorine emulsion solution for the dipping treatment, and the amount applied of the emulsion was adjusted to 7%. The obtained sheets had properties similar to those of the above sheets (Nos. 1 to 15).

EXAMPLE 2

Polystyrene beads having a particle size of 30 to 50 microns were incorporated into the same low density polyethylene as used in Example 1. A film having a thickness of 20 microns was prepared from the polystyrene bead-containing polyethylene by the T-die method. The film was then compressed to form a sheet having the properties shown in Table 1 (Run No. 16).

EXAMPLE 3

Zeolite having a particle of 15 to 40 microns, a bulk density of 0.36 g/cc and a pore volume of 1.4 cm³/g was incorporated in the same low density polyethylene as used in Example 1, and the zeolite-containing polyethylene was formed into a film and the film was compressed. The resulting sheet was dipped in a 2% solution of a fluorine type emulsion (FC-453-30 manufactured by Sumitomo-3 M). The amount applied of the emulsion was 7%. The properties of the obtained sheet are shown in Table 1 (Run No. 17).

TABLE 1

| Run No. | Filler Conditions | | | Compressing Conditions | | Properties | | |
|---|---|---|---|---|---|---|---|---|
| | Kind | Particle Size (μ) | Content (%) | Method[1] | Pressure (Kg/cm²) | Moisture Permeability[2] (g/cm²) | Water Pressure[3] Resistance (m) | Strength Ratio[4] (CD/MD) |
| 1 | glass | 44–60 | 10 | A | 25 | 0.13 | 1.2 | 1/1.05 |
| 2 | glass | 44–60 | 10 | A | 40 | 0.20 | 1.2 | 1/1.05 |
| 3 | glass | 44–60 | 10 | A | 60 | 0.30 | 1.1 | 1/1.15 |
| 4 | glass | 44–60 | 20 | A | 25 | 0.50 | 1.1 | 1/1.10 |
| 5 | glass | 44–60 | 20 | A | 40 | 0.71 | 1.1 | 1/1.10 |
| 6 | glass | 44–60 | 20 | A | 60 | 0.81 | 1.0 | 1/1.15 |
| 7 | glass | 44–60 | 30 | A | 25 | 0.63 | 1.1 | 1/1.10 |
| 8 | glass | 44–60 | 30 | A | 40 | 0.98 | 1.0 | 1/1.15 |
| 9 | glass | 44–60 | 30 | A | 60 | 1.25 | 1.0 | 1/1.20 |
| 10 | glass | 10–44 | 10 | B | 25 | 0.10 | 1.4 | 1/1.05 |
| 11 | glass | 10–44 | 10 | B | 40 | 0.31 | 1.1 | 1/1.05 |
| 12 | glass | 10–44 | 10 | B | 60 | 0.38 | 1.1 | 1/1.15 |
| 13 | glass | 44–60 | 10 | A | 25 | 0.14 | 1.2 | 1/1.05 |
| 14 | glass | 44–60 | 10 | A | 40 | 0.52 | 1.1 | 1/1.05 |
| 15 | glass | 44–60 | 10 | A | 60 | 0.62 | 1.1 | 1/1.15 |
| 16 | polystyrene | 30–50 | 20 | A | 100 | 0.08 | 1.4 | 1/1.05 |

TABLE 1-continued

| Run No. | Filler Conditions | | | Compressing Conditions | | Properties | | |
|---|---|---|---|---|---|---|---|---|
| | Kind | Particle Size (μ) | Content (%) | Method[1] | Pressure (Kg/cm²) | Moisture Permeability[2] (g/cm²) | Water Pressure[3] Resistance (m) | Strength Ratio[4] (CD/MD) |
| 17 | zeolite | 15–40 | 20 | B | 50 | 1.4 | 1.1 | 1/1.05 |

Note
[1] A designates the method shown in FIG. 6 and B designates the method shown in FIG. 7.
[2] The moisture (water vapor) permeability was determined according to the following procedures: 10 cc of distilled water was charged in a Petri dish having a diameter of 90 mm and a height of 20 mm, and the upper face of the dish was covered with the sample porous sheet and the periphery of the sheet was sealed by an adhesive tape of a vinyl resin. The weight W1 was measured. The dish was allowed to stand still in a thermostat chamber maintained at a temperature of 30° C. and a relative humidity of 65% for 2 hours. Then, the weight W2 was measured again. The moisture permeability W was calculated according to the following formula: $W = W1 - W2$
[3] JIS 1092
[4] ASTM D-882 (CD: strength in cross direction, MD: strength in machine direction)

From the results obtained in the foregoing Examples, it will readily be understood that according to the present invention, the moisture permeability can freely be controlled by changing the filler conditions and compression conditions without changing the water pressure resistance significantly.

The embodiments of the invention in which an exclusive property or privilege is claimed are defined as follows:

1. A liquid impermeable, vapor permeable, porous sheet consisting essentially of a thin, flexible sheet made of non-foamed thermoplastic resin, said sheet having fine pores distributed over the entire surface area of said sheet, said pores penetrating between and through the opposite surfaces of said sheet to permit permeation of vapor through said sheet, said pores being of a small size so that liquid cannot substantially permeate through said sheet, said pores each being defined by a cluster of fragments of broken-apart, frangible, filler particles wherein the cluster of fragments extends between said opposite surfaces of said sheet and defines margins of a passage extending between and through said opposite surfaces, the outermost fragments of said cluster being substantially flush with said opposite surfaces of said sheet.

2. A sheet as claimed in claim 1 containing from about 10 to 30 wt. % of said fragments, based on the weight of said sheet.

3. A sheet as claimed in claim 1 in which said thermoplastic resin is selected from the group consisting of polyethylene, nylon and polyester resin.

4. A sheet as claimed in claim 1 in which said filler particles are made of a material selected from the group consisting of glass, polystyrene, zeolite, silica, calcium carbonate, polypropylene, polytetrafluoroethylene and barium sulfate.

5. A sheet as claimed in claim 1 having a water-repellent material deposited thereon in an amount effective to increase the resistance of the sheet to the passing of water therethrough.

6. A sheet as claimed in claim 1 in which said flexible sheet is a film.

7. A disposable diaper having a backing sheet made of a sheet as claimed in claim 1.

* * * * *